United States Patent [19]

Morales et al.

[11] 4,270,526
[45] Jun. 2, 1981

[54] LINIMENT COMPOSITION AND APPLICATOR THEREFOR

[76] Inventors: Juan C. Morales, c/o George Spector, 3615 Woolworth Building, 233 Broadway; George Spector, 3615 Woolworth Building, 233 Broadway, both of, New York, N.Y. 10007

[21] Appl. No.: 934,840

[22] Filed: Aug. 18, 1978

[51] Int. Cl.³ .............................................. A61H 7/00
[52] U.S. Cl. ........................................ 128/67; 401/21
[58] Field of Search .................... 401/21, 22, 48, 218, 401/219, 220; 128/67; 15/360

[56] References Cited

U.S. PATENT DOCUMENTS

| 965,315 | 4/1910 | Moorhead | 15/369 |
| 3,289,240 | 12/1966 | Vanderveer et al. | 401/21 |

FOREIGN PATENT DOCUMENTS 2285837  4/1976  France ...................................... 401/21

OTHER PUBLICATIONS

"Pusey's Petrolatum Liniment" *Pharm. Formulas,* vol. I, Ed. 12, Pub. Chem. & Drugs (London, Eng.) 1953.

*Primary Examiner*—Robert W. Michell
*Assistant Examiner*—Thomas Wallen

[57] ABSTRACT

A liniment and an applicator for administering the same on a body skin, the liniment including as its ingredients: essential oil lily of the valley, essential oil Verbena, petroleum oil and essential oil Jasmin; the oils being possibly retailed in a kit for mixing by a consumer and including a dispensing applicator that massages the liniment into the skin.

1 Claim, 6 Drawing Figures

U.S. Patent  Jun. 2, 1981  4,270,526
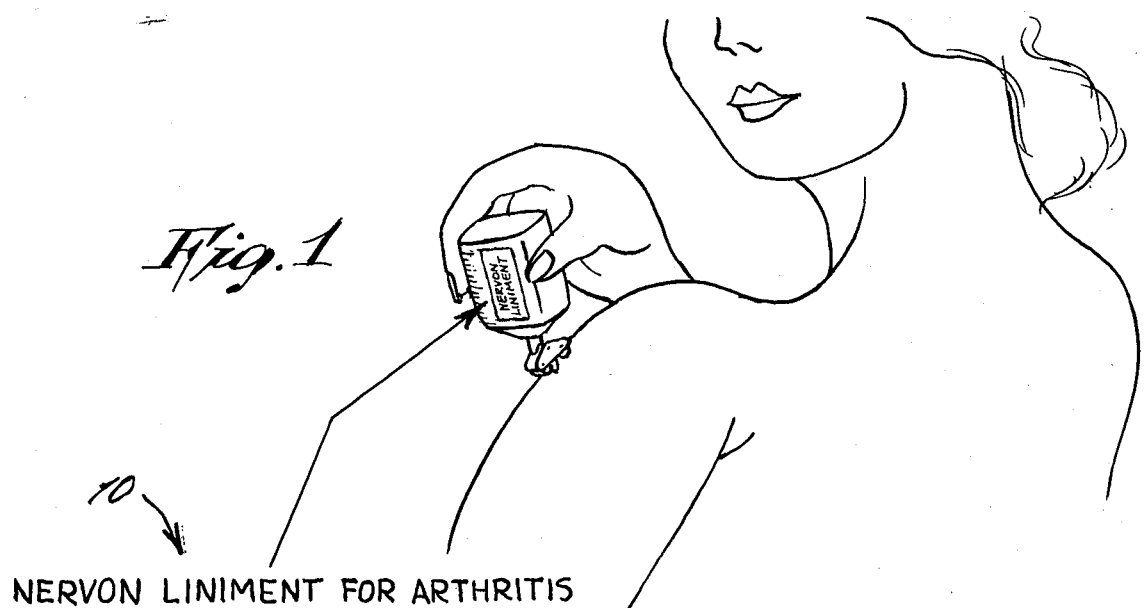
Fig. 1
NERVON LINIMENT FOR ARTHRITIS
CONSISTING OF
    ½ oz. ESSENTIAL OIL LILY OF THE VALLEY
    ¼ oz. ESSENTIAL OIL VERBENA
    5 oz. PETROLEUM OIL
    ¼ oz. ESSENTIAL OIL JASMIN
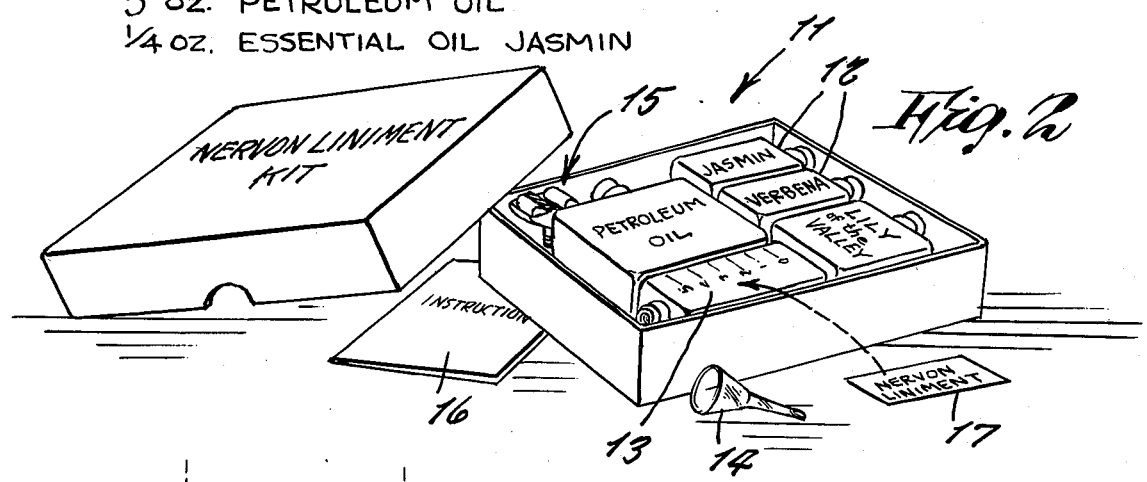
Fig. 2
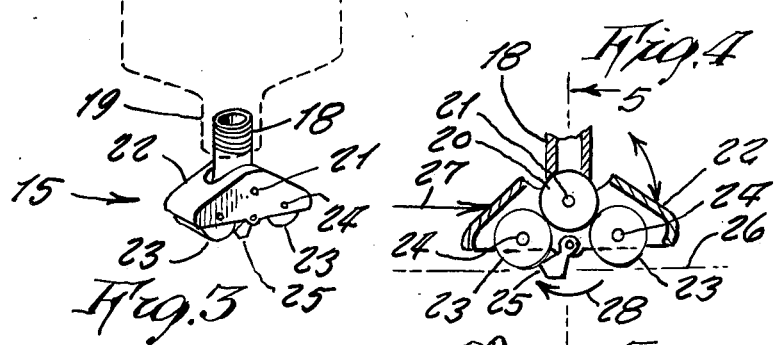
Fig. 3  Fig. 4  Fig. 5
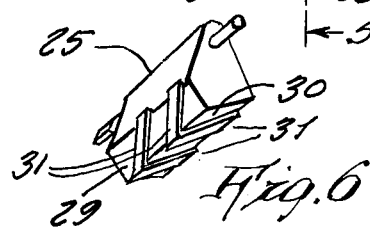
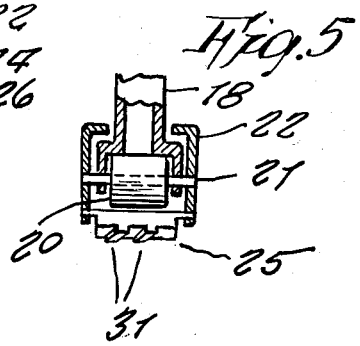
Fig. 6

LINIMENT COMPOSITION AND APPLICATOR THEREFOR

This invention relates generally to a liniment product and applicator.

A principal object of the present invention is to provide a liniment that is made of a mixture of four oils which are readily available.

Another object is to provide liniment, which can be made up in kits for allowing a person to mix the ingredients oneself.

Another object is to provide a massaging applicator for massaging the liniment into the afflicted area.

FIG. 1 is a view of the invention being applied to an arthritic area of a body and the figure identifying the invention ingredients.

FIG. 2 illustrates a kit for allowing a person to mix their own Nervon Liniment, and labeling the applicator bottle.

FIGS. 3 through 6 illustrate details of an applicator shown in FIG. 1, and which rolls the liniment on the body surface, the dispensing applicator being designed to automatically adjust for the applicator rollers to follow a changing contour of the body and also including a massaging bar which massages the body in opposite directions as it is rubbed back and forth over the skin surface.

Referring now to the drawing in greater detail, the reference numeral 10 represents a Nervon liniment for arthritis according to the present invention which is comprised of the following ingredients in the indicated relative proportions to each other:

| Essential Oil Lily of the Valley | ½ oz. |
| Essential Oil Verbena | ½ oz. |
| Petroleum Oil | 5 oz. |
| Essential Oil Jasmin | ½ oz. |

These ingredients are simply mixed together to form the liniment which is then applied to the body surface.

While the product may be sold as a completely prepared product for ready use, it may otherwise be also retailed in a form of a kit 11, as shown in FIG. 2, so a user can mix his own formula. Such kit can include separate bottles 12, each with one of the ingredients, a graduated bottle 13 in which the ingredients are poured by use of a funnel 14, and from which it may then be dispensed by an attached applicator 15. An instructions booklet 16 and a label 17 for affixing to the bottle 13 may also be included in the kit.

The applicator includes a spout 18 fixedly screwed to the bottle neck 19, and a roller 20 rotatable about pin 21 supported transversely through the spout, allows the roller to block the spout so that the liniment is dispensed by wetting the roller surface, and as the roller rotates the wetted surface thereof is exposed for application of the liniment thereupon. A hood 22 of hard plastic is supported pivotally free on the pin 21, and supports two additional rollers 23 on pins 24 and which engage the roller 20, so that the liniment is transferred from roller 20 to the rollers 23 that engage the skin surface of a person when applying liniment thereto. Thus the pivotable hood pivoted about pin 21 causes the rollers 23 to follow a body contour automatically without need to pivot the bottle 13 in the hand.

A massaging bar 25 is supported pivotally free on the hood so to pivot toward either roller 23, depending upon the direction into which the applicator is being pushed across the skin 26, as shown by arrows 27 and 28 in FIG. 4. The massaging bar includes flat faces 29 and 30 at an angle to each other and which are parallel to the skin during use, each face having projecting ribs 31 that rub into the skin while the liniment is being applied thereto so the massage the liniment in. The ribs extend angularly respective to a direction of travel of the applicator across the skin so to give a sideward pressure to the skin while moving thereacross. The ribs on one face are at opposite angle to the ribs on the other face, so that when the applicator travels in one direction, one face ribs applies sideward pressure to a right side direction and when the applicator travels in opposite direction the other face ribs apply sideward pressure in a left side direction, for resulting in a more thorough massage.

What is claimed is:

1. Body treatment apparatus comprising in combination a liniment and an applicator for applying said liniment, said applicator including a pair of rollers wetted with said liniment for rolling across a persons skin and a massaging bar pivotally mounted between said rollers that exerts opposite sideward pressure against said skin as said applicator travels reciprocally back and forth including a container for said liniment securable to said applicator cooperating with said rollers to distribute liniment on said rollers wherein the ingredients forming said liniment are contained in separate bottles of a kit that includes a graduated bottle into which said ingredients are mixed, a funnel for filling a neck of said graduated bottle, wherein said bottle is said container wherein said applicator includes a spout for affixing to said bottle neck, a rotatable roller at an end of said spout engaging said pair of rollers which are supported on a pivotable hood supported on said spout, said massaging bar being supported on said hood, and including a pair of faces each having angular extending ribs in different directions.

* * * * *